(12) United States Patent
Wang et al.

(10) Patent No.: US 11,471,872 B2
(45) Date of Patent: Oct. 18, 2022

(54) PURE PHASE ε/ε' IRON CARBIDE CATALYST FOR FISCHER-TROPSCH SYNTHESIS REACTION, PREPARATION METHOD THEREOF AND FISCHER-TROPSCH SYNTHESIS PROCESS

(71) Applicants: China Energy Investment Corporation Limited, Beijing (CN); National Institute of Clean-and-Low-Carbon Energy, Beijing (CN)

(72) Inventors: Peng Wang, Beijing (CN); Yijun Lv, Beijing (CN); Kui Zhagn, Beijing (CN); Fuguo Jiang, Beijing (CN); Zhuowu Men, Beijing (CN); Tao Wang, Beijing (CN); Qi Sun, Beijing (CN); Ping Miao, Beijing (CN)

(73) Assignees: China Energy Investment Corporation Limited, Beijing (CN); National Institute of Clean-and-Low-Carbon Energy, Beijing (CN)

( * ) Notice: Subject to any disclaimer, the term of this patent is extended or adjusted under 35 U.S.C. 154(b) by 112 days.

(21) Appl. No.: 17/044,688

(22) PCT Filed: Jun. 21, 2018

(86) PCT No.: PCT/CN2018/092189
§ 371 (c)(1),
(2) Date: Oct. 1, 2020

(87) PCT Pub. No.: WO2019/192080
PCT Pub. Date: Oct. 10, 2019

(65) Prior Publication Data
US 2021/0039081 A1    Feb. 11, 2021

(30) Foreign Application Priority Data

Apr. 2, 2018 (CN) .......................... 201810283708.0

(51) Int. Cl.
*B01J 37/18* (2006.01)
*B01J 27/22* (2006.01)
(Continued)

(52) U.S. Cl.
CPC ............... *B01J 37/18* (2013.01); *B01J 27/22* (2013.01); *B01J 35/023* (2013.01); *C10G 2/332* (2013.01)

(58) Field of Classification Search
CPC ........ B01J 37/18; B01J 27/22; B01J 35/1023; B01J 37/08; C10G 2/332; C01B 32/90; C01B 32/914
(Continued)

(56) References Cited

U.S. PATENT DOCUMENTS 2,535,042 A * 12/1950 Cohn ........................ B01J 27/22
501/87
2,562,806 A * 7/1951 Mayer ................... C07C 1/0445
518/720
(Continued)

FOREIGN PATENT DOCUMENTS

| CN | 104399501 | 3/2015 |
| CN | 105195189 | 12/2015 |

(Continued)

OTHER PUBLICATIONS

Kahyarian et al, "CO$_2$ corrosion of mild steel" *Trends in Oil and Gas Corrosion Research and Technologies*, 2017, pp. 149-190.
(Continued)

*Primary Examiner* — Patricia L. Hailey
(74) *Attorney, Agent, or Firm* — Conley Rose, P. C.; Brooks W Taylor

(57) ABSTRACT

The present disclosure relates to the field of Fischer-Tropsch synthesis reaction catalysts, and discloses a pure phase ε/ε' iron carbide catalyst for Fischer-Tropsch synthesis reaction, a preparation method thereof and a Fischer-Tropsch synthesis process, wherein the method comprises the following steps: (1) subjecting the nanometer iron powder or a nanopowder iron compound capable of obtaining the nanometer iron powder through in-situ reduction and $H_2$ to a surface purification treatment at the temperature of 250-510° C.; (2) pretreating the material obtained in the step (1) with $H_2$ and CO at the temperature of 80-180° C., wherein the molar ratio of $H_2$/CO is 1.2-2.8:1; (3) carrying out carbide preparation with the material obtained in the step (2), $H_2$ and CO at the temperature of 180-280° C., wherein the molar ratio of $H_2$/CO is 1.0-3.0:1. The preparation method has the advantages of simple and easily obtained raw materials, simple and convenient operation steps, being capable of preparing the 100% pure phase ε/ε' iron carbide catalyst having lower selectivity of $CO_2$ and $CH_4$ and higher selectivity of effective products.

16 Claims, 4 Drawing Sheets

(51) Int. Cl.
*B01J 35/02* (2006.01)
*C10G 2/00* (2006.01)

(58) Field of Classification Search
USPC .......... 502/177, 185; 423/439; 518/719, 720
See application file for complete search history.

(56) References Cited

U.S. PATENT DOCUMENTS

| | | | | |
|---|---|---|---|---|
| 2,780,537 A * | 2/1957 | Stelling | ............... | C21B 13/0033 423/439 |
| 3,885,023 A * | 5/1975 | Gray | ............... | B01J 27/22 423/439 |
| 4,842,759 A * | 6/1989 | Okamura | ............... | C01B 32/907 |
| 5,140,049 A * | 8/1992 | Fiato | ............... | C07C 1/12 518/700 |
| 5,366,897 A * | 11/1994 | Hager | ............... | B01J 8/1809 436/55 |
| 5,387,274 A * | 2/1995 | Dam G. | ............... | C21B 13/04 75/495 |
| 5,552,073 A * | 9/1996 | Tomiku | ............... | G11B 5/70615 |
| 5,618,032 A * | 4/1997 | Meissner | ............... | C21B 13/029 75/384 |
| 6,004,373 A * | 12/1999 | Hayashi | ............... | C21B 13/0073 75/505 |
| 8,809,225 B2 * | 8/2014 | Kharas | ............... | B01J 35/002 518/719 |
| 2004/0009871 A1 | 1/2004 | Hu et al. | | |
| 2012/0245236 A1 | 9/2012 | Suib et al. | | |
| 2014/0360917 A1 | 12/2014 | Park et al. | | |
| 2016/0096167 A1 | 4/2016 | Park et al. | | |
| 2021/0031174 A1* | 2/2021 | Wang | ............... | B01J 35/0013 |

FOREIGN PATENT DOCUMENTS

| | | |
|---|---|---|
| CN | 105728020 | 7/2016 |
| CN | 107442147 | 12/2017 |
| EA | 019736 | 2/2014 |
| EA | 028460 | 11/2017 |
| EP | 0361349 | 4/1990 |
| JP | 2008006406 | 1/2008 |
| KR | 20160104546 | 9/2016 |
| WO | WO 2012/135089 | 10/2012 |
| WO | WO2014/210089 | 12/2014 |
| WO | WO2017/103492 | 6/2017 |

OTHER PUBLICATIONS 10.2. Fischer-Tropsch Synthesis, *National Energy Technology Laboratory*, obtained from: https://www.netl.doc.gov/research/coal/energy-systems/gasification/gasifipedia/ftsynthesis—4 pages.

Chernavskii et al., "Size Effects in Carbidization of Iron Nanoparticles", Russian Journal of Physical Chemistry A, vol. 86, No. 8, Jun. 2012, pp. 1274-1280.

Liao et al., "Density functional theory study of CO adsorption on the (1 0 0),(0 0 1) and (0 1 0) surfaces of Fe3C", Journal of Molecular Catalysis A: Chemical, Elsevier, Amsterdam, NL, vol. 269, No. 1-2, Apr. 3, 2007, pp. 169-178.

Xu et al., "ε-Iron carbide as a low-temperature Fischer-Tropsch synthesis catalyst", Nature Communications, 5-5783, doi:10.1038/ncomms6783, Dec. 12, 2014, 8 pages.

PCT International Search Report and Written Opinion (with English translation) for corresponding PCT Application No. PCT/CN2018/092189, dated Jan. 3, 2019, 9 pages.

Santos et al. "Metal organic framework-mediated synthesis of highly active and stable Fischer-Tropsch catalysts," *Nature Communications*, Mar. 5, 2015—8 pages.

Smit et al., "Stability and reactivity of ε-χ-θ iron carbide catalyst phases in Fischer-Tropsch synthesis: Controlling μC," *Journal of the American Chemical Society (JACS)*, Vo. 132, No. 42, Oct. 6, 2010, pp. 14928-14941.

* cited by examiner

PURE PHASE ε/ε' IRON CARBIDE CATALYST FOR FISCHER-TROPSCH SYNTHESIS REACTION, PREPARATION METHOD THEREOF AND FISCHER-TROPSCH SYNTHESIS PROCESS

FIELD

The present disclosure relates to the field of Fischer-Tropsch synthesis reaction catalysts, in particular to a pure phase ε/ε' iron carbide catalyst for Fischer-Tropsch synthesis reaction, a preparation method thereof and a Fischer-Tropsch synthesis process.

BACKGROUND

The structure of primary energy in the People's Republic of China (PRC) is characterized by rich coal and insufficient oil and gas, the degree of dependence on the imported petroleum in China has continuously rising along with the rapid economic development, which reaches 61% in 2015, thereby severely impact the energy safety in China. Fischer-Tropsch synthesis can convert synthesis gas consisting of carbon monoxide and hydrogen into liquid fuels and chemicals, it has emerged as an increasingly important energy conversion pathway in recent years. The indirect coal liquefaction technology based on Fischer-Tropsch synthesis may be used for realizing clean utilization of coal and partially alleviating the problem that the China heavily depends on the imported petroleum, the technology has become one of the preferred technologies for replacing petroleum with coal and clean utilization of coal in China. Due to the industrial efforts for years, the iron-based coal indirect liquefaction technical industrial demonstration project with a production capacity of 160,000 tons/year has put into operation in China; in addition, the iron-based coal indirect liquefaction plants with a production capacity of 1 million tons/year invested by Shandong Yankuang Group and other companies and the iron-based coal indirect liquefaction plants with a production capacity of 4 million tons/year invested by Shenhua Ningxia Coal Industry Group Co., Ltd. have put into pilot run.

The reaction formulas for the Fischer-Tropsch synthesis are as follows:

$$(2n+1)H_2 + nCO \rightarrow C_nH_{2n+2} + nH_2O \quad (1)$$

$$2nH_2 + nCO \rightarrow C_nH_{2n} + nH_2O \quad (2)$$

Besides the final products alkanes and alkenes, the industrial Fischer-Tropsch synthesis can also produce the by-products carbon dioxide ($CO_2$) and methane ($CH_4$). The Fischer-Tropsch synthesis reaction has a complex mechanism and numerous steps, such as CO dissociation, carbon (C) hydrogenation, $CH_x$ chain growth, and the hydrogenation and dehydrogenation reactions which result in the desorption of hydrocarbon products and the removal of oxygen (O). From the viewpoint of practical application, the main purpose of improving the Fischer-Tropsch synthesis catalyst is to increase selectivity of the target products, reduce selectivity of the byproducts, enhance stability of the catalyst and prolong service life of the catalyst.

Iron is the cheapest transition metal used in the manufacture of Fischer-Tropsch synthesis catalysts. The active phase of iron-based Fischer-Tropsch catalysts is generally considered to be iron carbide. The traditional iron-based catalyst has high activity of water gas conversion ($CO+H_2O \rightarrow CO_2 + H_2$), so the traditional iron-based catalyst usually has high selectivity of a byproduct $CO_2$, which generally accounts for 25%-45% of the conversion raw material carbon monoxide. This is one of the major disadvantages of iron-based catalysts for the Fischer-Tropsch synthesis reaction.

It is difficult to synthesize the pure phase of iron carbide, which is the active phase of the iron-based Fischer-Tropsch synthesis catalyst. The active phase of the iron-based catalyst has very complicated variation, it causes considerable debates on the nature of the active phase and the Fischer-Tropsch synthesis reaction mechanism of the iron-based catalyst. The different carbides have been observed under the Fischer-Tropsch reaction conditions, including ε-$Fe_2C$, ε'-$Fe_{22}C$, $Fe_7C_3$, χ-$Fe_5C_2$ and θ-$Fe_3C$. The article "Stability and reactivity of ε-χ-θ iron carbide catalyst phases in Fischer-Tropsch synthesis: Controlling $\mu_C$" published on the top-level *Journal of the American Chemical Society (JACS)* in 2010 provides a systematic calculation and experiment of the conditions for generating the various iron carbides, as shown in FIG. 1, the occurrence of phase transition of iron carbides (ε-χ-θ phase transition) depends on the temperature and the $H_2$/CO ratio. Specifically, high temperature low carbon chemical potential ($\mu_C$), i.e., high $H_2$/CO ratio, generally results in preferential formation of iron carbide θ-$Fe_3C$; conversely, the high $\mu_C$ (low $H_2$/CO ratio) and moderate temperature (~250° C.) are conducive to formation of iron carbide χ-$Fe_5C_2$; the ε-carbide is preferentially formed at lower temperatures, higher carbon chemical potential $\mu_C$.

Its main viewpoint is as shown in FIG. 1, the article adopts $Fe_2O_3$ as an initiative precursor, a series of experiments are carried out in the Fischer-Tropsch synthesis reaction atmosphere, and the phase change of the product is tested by the X-ray Diffraction (XRD) and the synchrotron radiation in-situ X-ray Absorption Fine Structure Spectroscopy (XAS). At a higher carbon chemical potential $\mu_C$, the ε/ε' iron carbide needs to be generated and stably existed at a mild condition of ~200° C., and when the temperature is close to 250° C., the ε/ε' iron carbide is converted into χ-$Fe_5C_2$ which has a thermodynamic stability. In the industrial Fischer-Tropsch synthesis production, the iron-based Fischer-Tropsch synthesis temperature is within a range of 235-265° C., in order to increase the saturated vapor pressure of the byproduct steam, obtain high-quality steam and improve the economic benefit. In other words, the authoritative article indicates that the ε/ε' iron carbide is unstable at a temperature above 200° C., thus cannot be used as a catalyst suitable for the modern Fischer-Tropsch synthesis industry.

The article "Metal organic framework-mediated synthesis of highly active and stable Fischer-Tropsch catalysts" published in 2015 on *Nature communication*, a subsidiary of the top-level Journal *Nature*, provides an attempt of synthesizing the carbides, and successfully synthesizes χ-$Fe_5C_2$, which is a catalyst that can be used at the industrial temperatures of modern Fischer-Tropsch synthesis, however, its $CO_2$ selectivity is as high as 46%, which means that its theoretically maximum CO utilization efficiency is only 54%, the production efficiency is relatively low.

CN104399501A discloses a method for preparing ε-$Fe_2C$ nanoparticles suitable for low-temperature Fischer-Tropsch synthesis reaction. The initial precursor is a skeleton iron material, and the reaction system is intermittent discontinuous reaction of polyethylene glycol solvent. The catalyst has a $CO_2$ selectivity of 18.9% and a $CH_4$ selectivity of 17.3%. Its disadvantages are that the preparation method can only be applied at a low temperature less than 200° C., and the reaction cannot be continuously performed. It means that the catalyst is not suitable for continuous production under modern Fischer-Tropsch synthesis industrial conditions.

Among the aforementioned technologies, each has the problems such as complicated preparation process, expensive raw materials, poor catalyst stability, and excessively high selectivity of by-product $CO_2$ or $CH_4$.

SUMMARY

The present disclosure aims to overcome the aforementioned technical problems in the prior art and provides a pure phase ε/ε' iron carbide catalyst for Fischer-Tropsch synthesis reaction, a preparation method thereof and a Fischer-Tropsch synthesis process.

In order to achieve the above objects, a first aspect of the present disclosure provides a method of preparing a pure phase ε/ε' iron carbide catalyst for Fischer-Tropsch synthesis reaction, wherein the preparation method comprises the following steps:

(1) subjecting the nanometer iron powder or a nanometer powder iron compound capable of obtaining the nanometer iron powder through in-situ reduction and $H_2$ to a surface purification treatment at the temperature of 250-510° C.;

(2) pretreating the material obtained in the step (1) with $H_2$ and CO at the temperature of 80-180° C., wherein the molar ratio of $H_2$/CO is 1.2-2.8:1;

(3) carrying out carbide preparation with the material obtained in the step (2), $H_2$ and CO at the temperature of 180-280° C., wherein the molar ratio of $H_2$/CO is 1.0-3.0:1.

In a second aspect, the present disclosure provides a pure phase ε/ε' iron carbide catalyst for Fischer-Tropsch synthesis reaction obtained with the preparation method of the present disclosure.

In a third aspect, the present disclosure provides a Fischer-Tropsch synthesis process comprising: contacting a synthesis feed gas with a catalyst under the Fischer-Tropsch synthesis reaction conditions, wherein the catalyst is a pure phase ε/ε' iron carbide catalyst for Fischer-Tropsch synthesis reaction of the present disclosure.

The present disclosure can produce the following technical effects:

(1) The required raw materials are simple and easily available at low cost: the main raw material iron source is only the nanometer iron powder sold on the market, or the commercially available and ordinary nanometer iron oxide ($Fe_2O_3$) powder, nanometer magnetite ($Fe_3O_4$) powder, nanometer goethite powder, nanometer iron hydrate powder and other nanometer powder iron compounds which can be reduced in a Fischer-Tropsch synthesis reactor to generate nanometer iron; when the active phase carbide is synthesized, only the original reaction gas (carbon monoxide and $H_2$) of a reaction system is utilized; it does not involve with any inorganic or organic reaction raw material, such that the raw materials are greatly simplified compared with the prior art recited in the literatures;

(2) The operation steps are simple and convenient, and in the preferred embodiment, the catalyst preparation process and the Fischer-Tropsch synthesis process share the same reactor, so that any additional active phase carbide preparation reaction device is not required; the whole preparation process only needs three steps, namely the precursor surface purification, the pretreatment and the carbide preparation, the preparation and synthesis reaction of the active phase can be performed in situ in the same reactor.

(3) The present disclosure can be used for preparing the 100% purity active phase ε/ε' iron carbide, which is suitable for a high-temperature high-pressure (e.g., the temperature of 235-250° C., the pressure of 2.3-2.5 MPa, the high-carbon chemical potential $\mu_C$ with a ratio of $H_2$/CO=1.5-2.0) continuous reactor, the reaction stability is extremely high, such that the theoretical technical barrier in the traditional literature theory is broken through, namely "the ε/ε' iron carbide needs to be stably existed at a mild condition of less than 200° C. at a higher carbon chemical potential $\mu_C$", the stable temperature can be up to 250° C., and the selectivity of $CO_2$ is extremely low; under the reaction conditions of industrial Fischer-Tropsch synthesis, a high-pressure continuous reactor can be used for keeping continuous and stable reaction for more than 400 hours, and the selectivity of $CO_2$ is less than 8% (preferably, 5% or lower); in addition, the selectivity of the by-product $CH_4$ is kept at below 14% (preferably, lower than 11%), the selectivity of the effective product reaches 78% or more (preferably, 84% or more), and the preparation method is very suitable for the industrial and efficient production of oil wax products with the Fischer-Tropsch synthesis in modern coal chemical industry.

DETAILED DESCRIPTION

Figure 1:
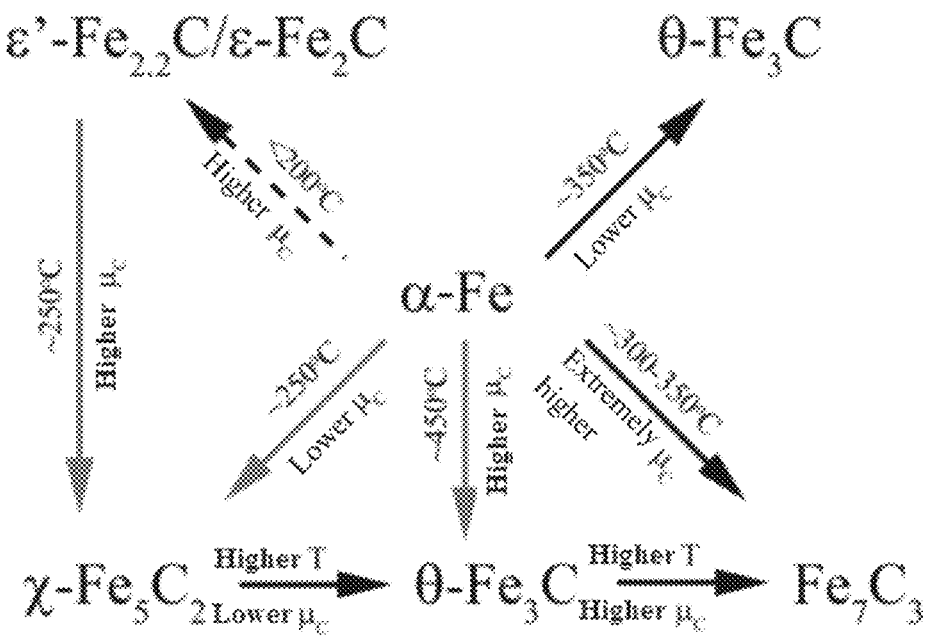
FIG. 1 shows a conversion relationship graph of the iron carbides in the prior art.

The terminals and any value of the ranges disclosed herein are not limited to the precise ranges or values, such ranges or values shall be comprehended as comprising the values adjacent to the ranges or values. As for numerical ranges, the endpoint values of the various ranges, the endpoint values and the individual point value of the various ranges, and the individual point values may be combined with one another to produce one or more new numerical ranges, which should be deemed have been specifically disclosed herein.

A first aspect of the present disclosure provides a method of preparing a pure phase ε/ε' iron carbide catalyst for Fischer-Tropsch synthesis reaction, wherein the preparation method comprises the following steps:

(1) subjecting the nanometer iron powder or a nanometer powder iron compound capable of obtaining the nanometer iron powder through in-situ reduction and $H_2$ to a surface purification treatment at the temperature of 250-510° C.;

(2) pretreating the material obtained in the step (1) with $H_2$ and CO at the temperature of 80-180° C., wherein the molar ratio of $H_2$/CO is 1.2-2.8:1;

(3) carrying out carbide preparation with the material obtained in the step (2), $H_2$ and CO at the temperature of 180-280° C., wherein the molar ratio of $H_2$/CO is 1.0-3.0:1.

In the preparation method of the present disclosure, the raw materials are simple and easily available with the low cost, wherein the nanometer iron powder may be conventionally selected in the technical field and can be a common product sold on the market, and the average grain diameter of the nanometer iron powder is preferably within a range of 4-30 nm, and more preferably 10-27 nm; the nano-powder iron compound may be a conventional choice in the field, and may be a common product sold on the market, for example, the nano-powder iron compound may be at least one selected from the group consisting of nanometer iron oxide powder, nanometer magnetite powder, nanometer goethite powder and nanometer iron hydrated oxide powder.

In the present disclosure, if the raw material in the step (1) is nanometer iron powder, the step (1) can play a role of surface purification treatment of the nanometer iron powder; if the raw material in step (1) is a nano-powder iron compound capable of obtaining the nanometer iron powder through in-situ reduction, the step (1) can simultaneously play the roles of in-situ generation of nanometer iron powder from the nano-powder iron compound and performing surface purification treatment of the generated nanometer iron powder.

In the present disclosure, the $H_2$ in step (1) may be introduced into the reaction system in the form of a flow of $H_2$, and the pressure of the surface purification treatment is controlled by controlling the pressure of the $H_2$ flow, it is preferable that in step (1), the pressure of the surface purification treatment is within a range of 0.1-15 atm, preferably 0.2-2.5 atm; the time is within a range of 0.5-8 h, preferably 1-7 h.

In the present disclosure, the amount of $H_2$ may be selected according to the amount of the raw material to be treated, and preferably, the gas velocity of $H_2$ in the step (1) is within a range of 500-20,000 mL/h/g, and more preferably 2,500-15,000 mL/h/g.

In the present disclosure, the $H_2$ and CO in the step (2) may pass through the reaction system in the form of ($H_2$+CO) mixed gas flow, and at the same time, the pressure of the pretreatment process is controlled by controlling the pressure of the ($H_2$+CO) mixed gas flow; it is preferable that in the step (2), the pressure of the pretreatment process is within a range of 0.05-7 atm, preferably 0.05-2.5 atm; the time is within a range of 15-90 min, preferably 25-75 min.

In the present disclosure, the gas velocity of $H_2$ and CO in the step (2) is preferably within a range of 200-8,000 mL/h/g, and more preferably 1,000-6,500 mL/h/g.

In the present disclosure, the $H_2$ and CO in step (3) may pass through the reaction system in the form of ($H_2$+CO) mixed gas flow, and at the same time, the pressure of the carbide preparation process is controlled by controlling the pressure of the ($H_2$+CO) mixed gas flow, preferably, the pressure of the carbide preparation in the step (3) is within a range of 0.09-10 atm, preferably 0.15-3 atm; the time is within a range of 0.5-10 h, preferably 1.5-8 h;

In the present disclosure, the gas velocity of $H_2$ and CO in the step (3) is preferably within a range of 200-20,000 mL/h/g, and more preferably 4,000-15,000 mL/h/g.

In the present disclosure, it is preferable that the molar ratio of $H_2$/CO in the step (2) is larger than the molar ratio of $H_2$/CO in the step (3).

Unless otherwise specified in the present disclosure, the term "mL/h/g" refers to a volume of feed gas per grain of raw material per hour.

According to a preferred embodiment of the present disclosure, the preparation method further comprises: the system temperature after the pretreatment is increased to 180-280° C. at the temperature rise rate of 0.2-5° C./min. In the preferred embodiment, the prepared pure phase ε/ε' iron carbide catalyst may have a better effective product selectivity in the Fischer-Tropsch synthesis reaction. Further preferably, the system temperature after the pretreatment is increased to 200-270° C. at the temperature rise rate of 0.2-2.5° C./min.

According to another preferred embodiment of the present disclosure, the surface purification treatment, pretreatment and carbide preparation process is carried out in a Fischer-Tropsch synthesis reactor. In the preferred embodiment, the catalyst preparation and the Fischer-Tropsch synthesis share the same reactor, such that the $H_2$ and CO raw materials in the catalyst preparation process may be the original raw materials of the Fischer-Tropsch synthesis reaction system, an additional active phase carbide preparation reaction device is not required; the whole preparation process may allow that the preparation and synthesis reaction of the active phase can be performed in situ in the same reactor, and the operation steps are more simple and convenient.

In a second aspect, the present disclosure provides a pure phase ε/ε' iron carbide catalyst for Fischer-Tropsch synthesis reaction obtained with the preparation method of the present disclosure. The pure phase ε/ε' iron carbide catalyst is the active phase ε/ε' iron carbide with 100% pure phase.

In a third aspect, the present disclosure provides a Fischer-Tropsch synthesis process comprising: contacting a synthesis feed gas with a catalyst under the Fischer-Tropsch synthesis reaction conditions, wherein the catalyst is a pure phase ε/ε' iron carbide catalyst for Fischer-Tropsch synthesis reaction of the present disclosure.

The pure phase ε/ε' iron carbide catalyst is used as a catalyst for Fischer-Tropsch synthesis, and can carry out Fischer-Tropsch synthesis reaction under high temperature and high pressure, for example, the Fischer-Tropsch synthesis reaction conditions comprise: the temperature is within a range of 235–250° C., and the pressure is within a range of 2.3-2.5 MPa.

Unless otherwise specified in the present disclosure, the pressure refers to an absolute pressure.

In the present disclosure, it is preferable that the Fischer-Tropsch synthesis reaction is carried out in a high temperature and high pressure continuous reactor. The pure phase ε/ε' iron carbide catalyst may allow that the Fischer-Tropsch synthesis reaction is continuously and stably carried out for more than 400 hours in a high-temperature high-pressure continuous reactor.

The present disclosure will be described in detail below with reference to examples. In the following examples, CO conversion rate %=[(mole number of CO in the feedstock−mole number of CO in the discharged material)/mole number of CO in the feedstock]×100%;

$CO_2$ selectivity %=[mole number of $CO_2$ in the discharged material/(mole number of CO in the feedstock−mole number of CO in the discharged material)]×100%;

$CH_4$ selectivity %=[mole number of $CH_4$ in the discharged material/(mole number of CO in the feedstock×CO conversion rate % (1−$CO_2$ selectivity %))]×100%;

Effective product selectivity %=[1−$CO_2$ Selectivity %−$CH_4$ Selectivity %]×100%.

Example 1

The example served to illustrate the preparation of a pure phase ε/ε' iron carbide catalyst. (For the sake of facilitating comparison, all the raw materials were derived from the same company, but the raw materials were not limited to the company during the actual operation).

(1) 1.00 g of nanometer iron powder (from the Alfa Reagent Company, CAS No. 7439-89-6) with an average grain diameter range of 21±6 nm was weighted, and the nanometer iron powder was named as a precursor 1;

(2) The precursor 1 was put into a tubular Fischer-Tropsch synthesis reactor, and the $H_2$ flow having a gas velocity of 2,500 mL/h/g and a pressure of 2.5 atm was introduced at the temperature of 250° C. to react for 7 hours;

(3) The temperature in the reactor was reduced to 180° C., and the $H_2$ flow was switched to the ($H_2$+CO) gas flow having a molar ratio of $H_2$/CO=1.2, a gas velocity of 6,500 ml/h/g and a total pressure of 0.05 atm, and the pretreatment reaction was carried out for 75 min;

(4) The gas flow in the reactor was switched to the ($H_2$+CO) gas flow having a molar ratio $H_2$/CO=1.0, a gas velocity of 4,000 mL/h/g and a total pressure of 3 atm, in the meanwhile, the temperature was steadily raised to 200° C. at a temperature rise rate of 0.2° C./min, the temperature was maintained for 1.5 h. The preparation of the pure phase ε/ε' iron carbide catalyst was completed, the catalyst was marked as the ε/ε' iron carbide catalyst A1.

Figure 2:
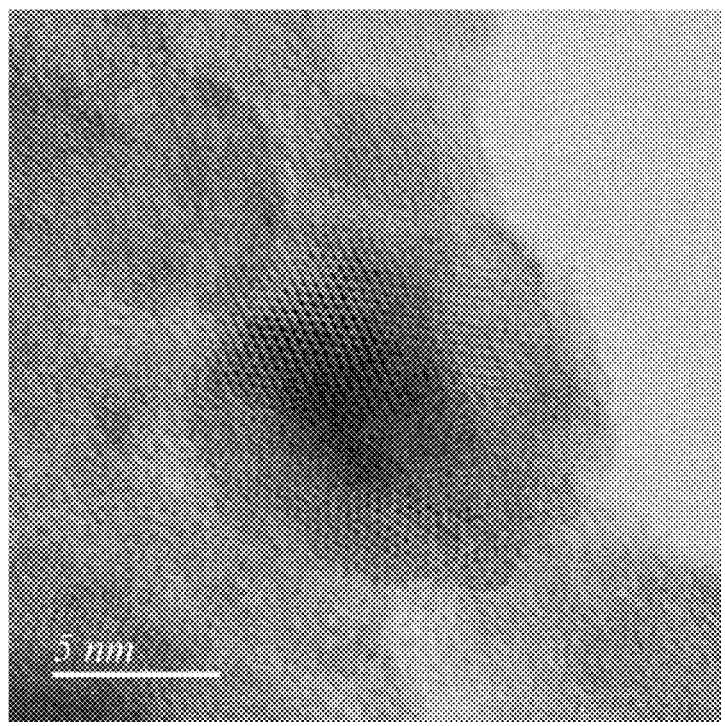
FIG. 2 illustrates a Transmission Electron Microscopy (TEM) image of the precursor 1 in Example 1.
Figure 3:
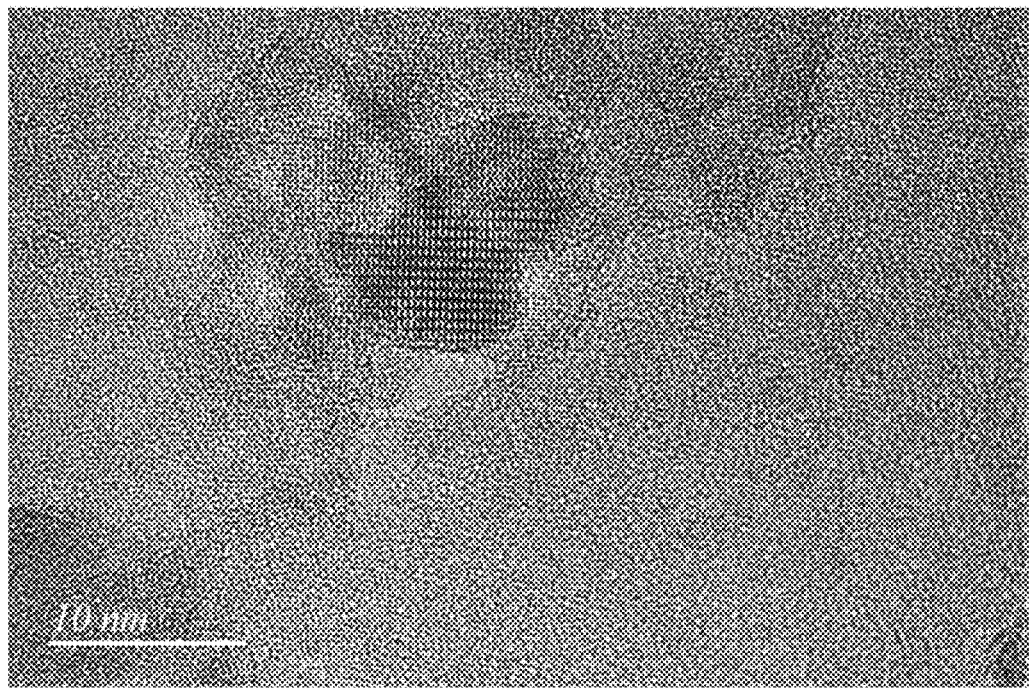
FIG. 3 illustrates a high resolution transmission electron microscope (HRTEM) image of the precursor 1 in Example 1.

Testing:

The precursor 1 was taken and subjected to Transmission Electron Microscopy (TEM) and High Resolution Transmission Electron Microscopy (HRTEM) measurements, and the measurement results were shown in FIG. 2 and FIG. 3 respectively.

Figure 4:
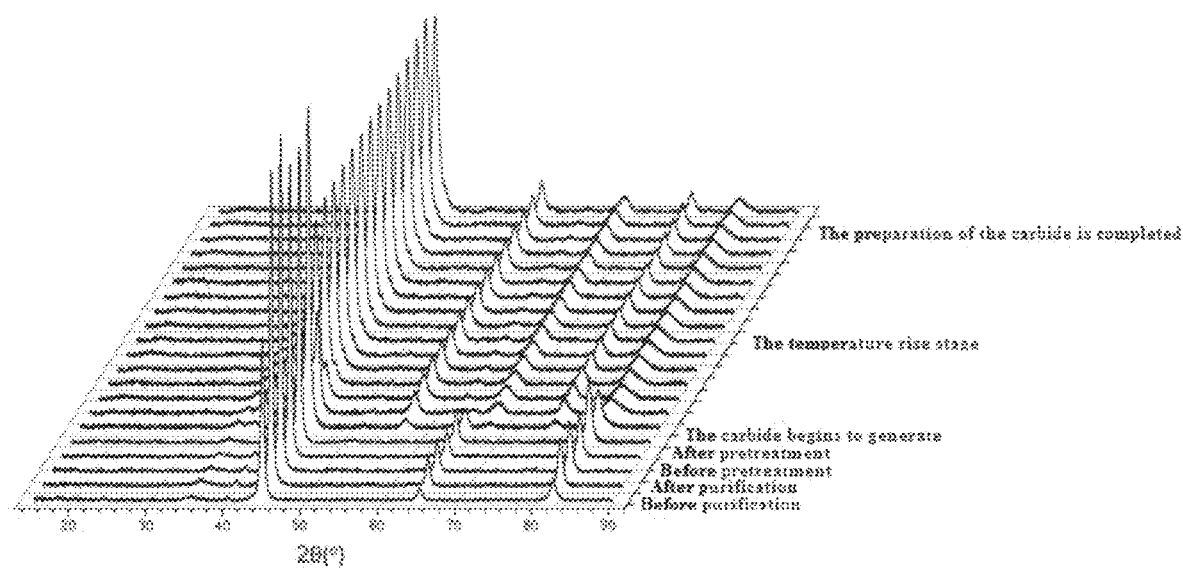
FIG. 4 shows an in situ X-ray Diffraction (XRD) pattern of the preparation of ε/ε' iron carbide catalyst A of Example 1.
Figure 5:
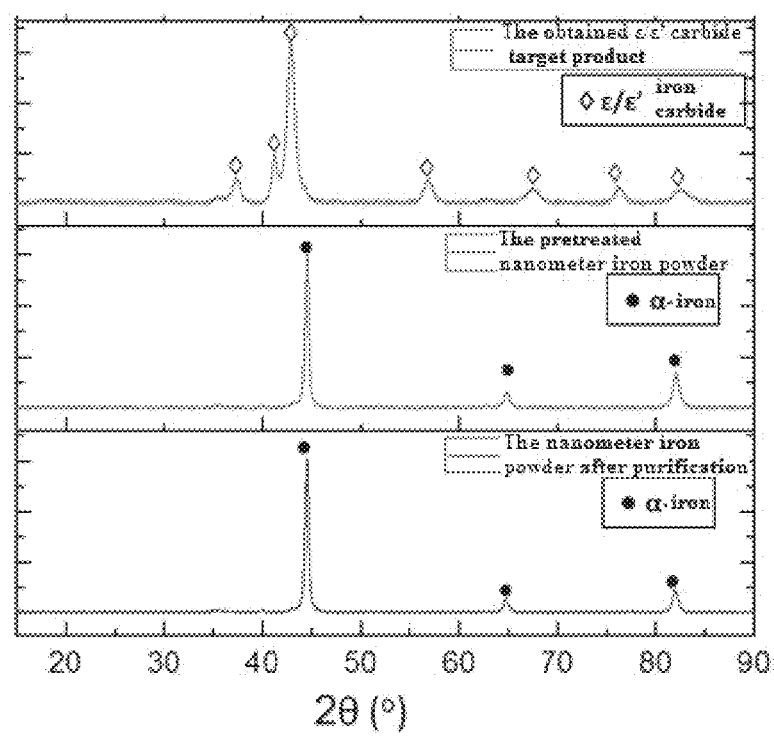
FIG. 5 illustrates an in situ XRD pattern of ε/ε' iron carbide catalyst A obtained in Example 1.

The in situ XRD detection technique was adopted, that is, the aforementioned catalyst preparation process was carried out while monitoring the change of crystalline phase of the materials using an X-ray Diffractometer (the XFD was commercially available from Rigaku Corporation, model D/max-2600/PC), the results were shown in FIG. 4 and FIG. 5.

Wherein the conversion process from the nanometer iron powder to the target carbide was clearly visible in FIG. 4; as can be seen from FIG. 5, the prepared target product ε/ε' iron carbide illustrated the desirable crystallinity, the product ε/ε' iron carbide perfectly corresponded to all characteristic peaks of the ε/ε' iron carbide, the purity was extremely high, and the product did not contain any other impurity.

An in-situ Mossbauer spectrum detection technology was adopted, namely a Mossbauer spectrum (Transmission $^{57}$Fe, $^{57}$Co (Rh) source sinusoidal velocity spectrometer) was used for monitoring the component change of the materials during the preparation process, a treatment method for adding 250° C. saturated vapor pressure water steam into reaction gas was performed on the target product active phase ε/ε' iron carbide, such that the condition after long-period operation under the industrial conditions was simulated. The change process from the precursor 1 to the target carbide and the situation after long-term operation under the simulated industrial conditions through high-temperature water vapor treatment were clearly visible through the in-situ Mossbauer spectrum monitoring. The results were illustrated in FIG. 6 and Table 1.

Figure 6:
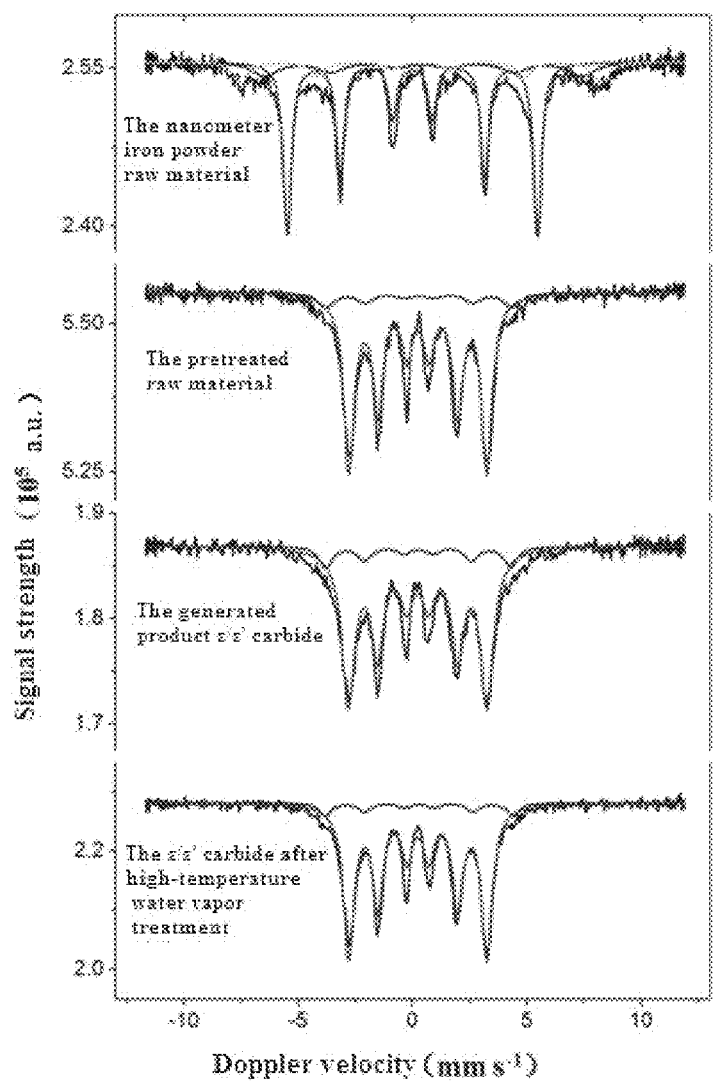
FIG. 6 illustrates an in situ Mossbauer spectrogram of the preparation process of ε/ε' iron carbide catalyst A in Example 1.

FIG. 6 clearly illustrated the process of the nanometer iron powder to the target carbide and the process of subjecting to the high-temperature water vapor treatment.

Table 1 showed the statistics of specific data of phase transformation, the purity of the active phase ε/ε' iron carbide in the target product prepared in Example 1 was 100%, and the purity was still 100% after long-term operation under simulated industrial conditions, as illustrated in Table 1. It demonstrated that the method of the present disclosure can be used for preparing a supported catalyst of active phase ε/ε' iron carbide with a purity of 100%, and the supported ε/ε' iron carbide catalyst obtained with the preparation method of the present disclosure can stably exist at a high temperature of 250° C., and furthermore, the ε/ε' iron carbide catalyst can still maintain 100% purity even after the corrosion of the simulated industrial high temperature and high pressure water steam.

TABLE 1

| Treatment conditions | Phase | Molar content of the phase |
|---|---|---|
| The purified raw material | $Fe^0$ | 83% |
|  | $Fe^{3+}$ | 17% |
| The pretreated raw material | ε'-$Fe_{2.2}$C/ε-$Fe_2$C | 100% |
| The prepared product ε/ε' iron carbide | ε'-$Fe_{2.2}$C/ε-$Fe_2$C | 100% |
| The ε/ε' iron carbide after long-period operation under the simulated industrial conditions | ε'-$Fe_{2.2}$C/ε-$Fe_2$C | 100% |

Example 2

The example served to illustrate the preparation of a pure phase ε/ε' iron carbide catalyst.

(1) 1.00 g of nanometer magnetite ($Fe_3O_4$) powder (from the Alfa Reagent Company, CAS No. 1317-61-9) with an average grain diameter range of 17±7 nm was weighted, and the nanometer magnetite was named as a precursor 2;

(2) The precursor 2 was put into a tubular Fischer-Tropsch synthesis reactor, and the $H_2$ flow having a gas velocity of 15,000 mL/h/g and a pressure of 0.2 atm was introduced at the temperature of 510° C. to react for 1 hour;

(3) The temperature in the reactor was reduced to 80° C., and the $H_2$ flow was switched to the ($H_2$+CO) gas flow having a molar ratio of $H_2$/CO=2.8, a gas velocity of 1,000 ml/h/g and a total pressure of 2.5 atm, and the pretreatment reaction was carried out for 25 min;

(4) The gas flow in the reactor was switched to the ($H_2$+CO) gas flow having a molar ratio $H_2$/CO=3.0, a gas velocity of 15,000 ml/h/g and a total pressure of 0.15 atm, in the meanwhile, the temperature was steadily raised to 270° C. at a temperature rise rate of 2.5° C./min, the temperature was maintained for 8 h. The preparation of the pure phase ε/ε' iron carbide catalyst was completed, the catalyst was marked as the ε/ε' iron carbide catalyst A2.

Example 3

The example served to illustrate the preparation of a pure phase ε/ε' iron carbide catalyst.

(1) 1.00 g of nanometer goethite (alpha-FeO(OH)) powder (from the Alfa Reagent Company, CAS No. 20344-49-4) with an average grain diameter range of 19±7 nm was weighted, and the nanometer goethite was named as a precursor 3;

(2) The precursor 3 was put into a tubular Fischer-Tropsch synthesis reactor, and the $H_2$ flow having a gas velocity of 5,000 mL/h/g and a pressure of 1.3 atm was introduced at the temperature of 470° C. to react for 5 hours;

(3) The temperature in the reactor was reduced to 137° C., and the $H_2$ flow was switched to the ($H_2$+CO) gas flow having a molar ratio of $H_2$/CO=2.4, a gas velocity of 5,000 ml/h/g and a total pressure of 0.1 atm, and the pretreatment reaction was carried out for 50 min;

(4) The gas flow in the reactor was switched to the (H$_2$+CO) gas flow having a molar ratio H$_2$/CO=2.5, a gas velocity of 10,000 mL/h/g and a total pressure of 2 atm, in the meanwhile, the temperature was steadily raised to 240° C. at a temperature rise rate of 1° C./min, the temperature was maintained for 4 h. The preparation of the pure phase ε/ε' iron carbide catalyst was completed, the catalyst was marked as the ε/ε' iron carbide catalyst A3.

Example 4

A pure phase ε/ε' iron carbide catalyst was prepared according to the method of Example 1, except that in step (2), the pressure of the H$_2$ flow was 15 atm. The ε/ε' iron carbide catalyst A4 was prepared.

Example 5

A pure phase ε/ε' iron carbide catalyst was prepared according to the method of Example 1, except that in step (2), the gas velocity of H$_2$ flow was 500 mL/h/g. The ε/ε' iron carbide catalyst A5 was prepared.

Example 6

A pure phase ε/ε' iron carbide catalyst was prepared according to the method of Example 1, except that in step (3), the pressure of the (H$_2$+CO) gas flow was 7 atm. The ε/ε' iron carbide catalyst A6 was prepared.

Example 7

A pure phase ε/ε' iron carbide catalyst was prepared according to the method of Example 1, except that in step (3), the gas velocity of the (H$_2$+CO) gas flow was 200 ml/h/g. The ε/ε' iron carbide catalyst A7 was prepared.

Example 8

A pure phase ε/ε' iron carbide catalyst was prepared according to the method of Example 1, except that in step (4), the pressure of the (H$_2$+CO) gas flow was 0.09 atm. The ε/ε' iron carbide catalyst A8 was prepared.

Example 9

A pure phase ε/ε' iron carbide catalyst was prepared according to the method of Example 1, except that in step (4), the gas velocity of the (H$_2$+CO) gas flow was 200 mL/h/g. The ε/ε' iron carbide catalyst A9 was prepared.

Example 10

A pure phase ε/ε' iron carbide catalyst was prepared according to the method of Example 1, except that in step (4), the temperature rise rate was 5° C./min. The ε/ε' iron carbide catalyst A10 was prepared.

Comparative Example 1

A pure phase ε/ε' iron carbide catalyst was prepared according to the method of Example 1, except that the material obtained in the step (2) was directly treated according to the step (4) without performing the step (3). The iron carbide catalyst D1 was prepared.

Comparative Example 2

A pure phase ε/ε' iron carbide catalyst was prepared according to the method of Example 1, except that in step (3), the molar ratio of H$_2$/CO was 1.1. The iron carbide catalyst D2 was prepared.

Comparative Example 3

A pure phase ε/ε' iron carbide catalyst was prepared according to the method of Example 1, except that in step (4), the molar ratio of H$_2$/CO was 0.9. The iron carbide catalyst D3 was prepared.

Comparative Example 4

A pure phase ε/ε' iron carbide catalyst was prepared according to the method of Example 1, except that the pretreatment temperature in step (3) was 200° C., and the temperature of carbide preparation in step (4) was 290° C. The iron carbide catalyst D4 was prepared.

Comparative Example 5

The comparative example served to illustrate a method for preparing iron carbide catalysts in the prior art (N. Lohitharn et al./*Journal of Catalysis* 255 (2008) 104-113).

(1) According to the molar ratio of 100Fe/5Cu/17Si, 0.6 mol/L of Fe(NO$_3$)$_3$.9H$_2$O and CuN$_2$O$_6$.3H$_2$O in the raw materials were mixed, 60 ml of H$_2$O was added for dissolution, another ingredient Si(OC$_2$H$_5$)$_4$ was taken and added into 40 ml of propanol for dissolution. The two solutions obtained above were mixed, and heated to a temperature of 83±3° C.;

(2) 2.7 mol/L NH$_4$OH solution was preheated to 83±3° C.;

(3) The NH$_4$OH solution obtained in the step (2) was continuously added into the mixed solution obtained in the step (1), and the blended solution was stirred vigorously until a precipitate was generated, wherein the pH=8-9 was maintained at the end point of the precipitation. The precipitation was subjected to aging at room temperature for 17 hours, and washed thoroughly with 1.3-1.5 L deionized water to remove NH$_3$ till pH=7-8. The washed precipitate was subjected to drying at 110° C. for 18-24 hours, and calcinating at 300° C. in air for 5 hours, and was cooled to room temperature within 2 hours;

(4) The material with a particle size less than 90 μm was sieved, and subjected to activation under the typical industrial catalyst activation conditions consisting of a H$_2$/CO molar ratio of 1.0, a total gas velocity of 5,000 mL/h/g, and a temperature of 260° C. for 12 h, the iron carbide catalyst D5 was prepared.

Test Example (1) The Mossbauer spectroscopy was used to measure the molar content of the ε'-Fe$_{22}$C/ε-Fe$_2$C phases in the active phases of the product catalysts A2-A10 and D1-D5, respectively. The results were shown in Table 2.

(2) Under the conditions consisting of a molar ratio of reaction gases H$_2$/CO=1.5, a pressure 2.5 MPa, a temperature 240° C. and a total gas velocity (H$_2$+CO) of 20,000 ml/h/g, the product catalysts A1-A10 and D1-D5 were respectively contacted with the reaction gases H$_2$ and CO to carry out the Fischer-Tropsch synthesis reaction. The catalyst activity and product selectivity of the catalysts were monitored at 10 h and 400 h of reaction. The results were shown in Table 3.

prepared with the method of the present disclosure is significantly superior to that of the iron carbide catalyst in the prior art.

TABLE 2

|  | A1 | A2 | A3 | A4 | A5 | A6 | A7 | A8 |
|---|---|---|---|---|---|---|---|---|
| $\varepsilon'$-$Fe_{2.2}C$/$\varepsilon$-$Fe_2C$ molar content | 100% | 100% | 100% | 100% | 100% | 100% | 100% | 100% |

|  | A9 | A10 | D1 | D2 | D3 | D4 | D5 |
|---|---|---|---|---|---|---|---|
| $\varepsilon'$-$Fe_{2.2}C$/$\varepsilon$-$Fe_2C$ molar content | 100% | 100% | 58% | 67% | 70% | 74% | 18% |

As can be seen from the results of Table 2, the pure phase $\varepsilon/\varepsilon'$ iron carbide can be produced with the preparation method of the present disclosure.

TABLE 3

| Reaction time, h | CO conversion rate mmol/h/g-Fe. | | $CO_2$ selectivity %* | | $CH_4$ selectivity % | | Effective product selectivity %# | |
|---|---|---|---|---|---|---|---|---|
|  | 10 | 400 | 10 | 400 | 10 | 400 | 10 | 400 |
| A1 | 80.8 | 80.2 | 3.0 | 3.5 | 9.8 | 9.6 | 87.2 | 86.9 |
| A2 | 72.8 | 72.5 | 4.9 | 4.6 | 10.7 | 10.9 | 84.4 | 84.5 |
| A3 | 69.5 | 70.0 | 4.5 | 4.4 | 10.1 | 10.4 | 85.4 | 85.2 |
| A4 | 54.3 | 52.2 | 6.7 | 6.5 | 10.5 | 10.7 | 82.8 | 82.8 |
| A5 | 51.1 | 50.8 | 7.3 | 7.7 | 13.2 | 13.5 | 79.5 | 78.8 |
| A6 | 54.6 | 54 | 8 | 7.8 | 11.1 | 11.4 | 80.9 | 80.8 |
| A7 | 49.7 | 49.4 | 6.5 | 6.7 | 12.4 | 12.4 | 81.1 | 80.9 |
| A8 | 49.9 | 50.3 | 7.1 | 7.1 | 12.3 | 12.7 | 80.6 | 80.2 |
| A9 | 53.6 | 52 | 5.3 | 5.1 | 11.7 | 11.3 | 83 | 83.6 |
| A10 | 55.7 | 54.2 | 6 | 6.4 | 9.1 | 9.5 | 84.9 | 84.1 |
| D1 | 41.8 | 37.7 | 17.6 | 19.1 | 15.1 | 16.7 | 67.3 | 64.2 |
| D2 | 42.7 | 39.5 | 21.2 | 23 | 14.7 | 15.7 | 64.1 | 61.3 |
| D3 | 45.4 | 36.4 | 24.1 | 26.1 | 12.4 | 15.6 | 63.5 | 58.3 |
| D4 | 40.7 | 38.5 | 23.4 | 25.5 | 16 | 19.1 | 60.6 | 55.4 |
| D5 | 35.3 | 30.6 | 29.2 | 34.1 | 19.1 | 23.3 | 51.7 | 42.6 |

Note:
*each of the aforementioned selectivities is based on the total CO conversion amount;

Notes:
the effective product selectivity refers to the selectivity of products other than the by-products $CO_2$ and $CH_4$.

As can be seen from the results of table 3, the pure phase $\varepsilon/\varepsilon'$ iron carbide catalyst prepared with the method of the present disclosure exhibits ultra-low $CO_2$ selectivity under the industrial conditions, preferably, the $CO_2$ selectivity may be lower than 5%; in contrast, the $CO_2$ selectivity of the iron carbide catalyst D5 prepared by the prior art under the same industrial conditions is as high as 29.2%-34.1%.

Moreover, the $CH_4$ selectivity of the pure phase $\varepsilon/\varepsilon'$ iron carbide catalyst prepared with the method of the present disclosure is lower than 14% (preferably lower than 11%), and the selectivity of effective products can reach 78% or more (preferably reach 84% or more); the iron carbide catalyst D5 prepared by the prior art has high $CH_4$ selectivity, the effective product selectivity is only 51.7%, thus the CO utilization efficiency is low.

Finally, the experimental data at an elapse of the 10 hour and the 400 hour are compared, the results reveals that the pure phase $\varepsilon/\varepsilon'$ iron carbide catalyst prepared with the method disclosed by the present disclosure keeps stable and shows no obvious change in both the CO conversion rate and the product selectivity after reacting for 400 hours; however, various parameters of the iron carbide catalyst D5 prepared by the prior art are obviously degraded, it demonstrates that the stability of the pure phase $\varepsilon/\varepsilon'$ iron carbide catalyst The above content describes in detail the preferred embodiments of the present disclosure, but the present disclosure is not limited thereto. A variety of simple modifications can be made in regard to the technical solutions of the present disclosure within the scope of the technical concept of the present disclosure, including a combination of individual technical features in any other suitable manner, such simple modifications and combinations thereof shall also be regarded as the content disclosed by the present disclosure, each of them falls into the protection scope of the present disclosure.

The invention claimed is:

1. A method of preparing a pure phase $\varepsilon/\varepsilon'$ iron carbide catalyst for Fischer-Tropsch synthesis reaction, wherein the preparation method comprises the following steps:
   (1) subjecting a nanometer iron powder or a nanometer powder iron compound capable of obtaining the nanometer iron powder through in-situ reduction and $H_2$ to a surface purification treatment at the temperature of 250-510° C.;
   (2) pretreating a material obtained in the step (1) with $H_2$ and CO at the temperature of 80-180° C., wherein the molar ratio of $H_2$/CO is 1.2-2.8:1; and
   (3) carrying out carbide preparation with the material obtained in the step (2), $H_2$ and CO at the temperature of 180-280° C., wherein the molar ratio of $H_2$/CO is 1.0-3.0:1.

2. The method of claim 1, wherein the nanometer powder iron compound is at least one selected from a group consisting of nanometer iron oxide powder, nanometer magnetite powder, nanometer goethite powder, and nanometer iron hydrated oxide powder.

3. The method of claim 1, wherein an average grain diameter of the nanometer iron powder is within a range of 4-30 nm.

4. The method of claim 3, wherein the average grain diameter of the nanometer iron powder is within a range of 10-27 nm.

5. The method of claim 1, wherein in the step (1), a pressure of the surface purification treatment is within a range of 0.1-15 atm; a time is within a range of 0.5-8 h; and a gas velocity of $H_2$ in the step (1) is within a range of 500-20,000 mL/h/g.

6. The method of claim 5, wherein in the step (1), the pressure of the surface purification treatment is within a range of 0.2-2.5 atm; the time is within a range of 1-7 h; and the gas velocity of $H_2$ in the step (1) is within a range of 2,500-15,000 mL/h/g.

7. The method of claim 1, wherein in the step (2), a pressure of a pretreatment process is within a range of 0.05-7 atm; a time is within a range of 15-90 min; a gas velocity of $H_2$ and CO in the step (2) is within a range of 200-8,000 mL/h/g.

8. The method of claim 7, wherein in the step (2), the pressure of the pretreatment process is within a range of 0.05-2.5 atm; the time is within a range of 25-75 min; and the gas velocity of $H_2$ and CO in the step (2) is within a range of 1,000-6,500 mL/h/g.

9. The method of claim 1, wherein in the step (3), a pressure of the carbide preparation is within a range of 0.09-10 atm; a time is within a range of 0.5-10 h; and a gas velocity of $H_2$ and CO in the step (3) is within a range of 200-20,000 mL/h/g.

10. The method of claim 9, wherein in the step (3), the pressure of the carbide preparation is within a range of 0.15-3 atm; the time is within a range of 1.5-8 h; and the gas velocity of $H_2$ and CO in the step (3) is within a range of 4,000-15,000 mL/h/g.

11. The method of claim 1, wherein the method further comprises: a system temperature after the pretreatment is increased to 180-280° C. at a temperature rise rate of 0.2-5° C./min.

12. The method of claim 11, wherein the system temperature after the pretreatment is increased to 200-270° C. at the temperature rise rate of 0.2-2.5° C./min.

13. The method of claim 1, wherein the surface purification treatment, pretreating, and carbide preparation is carried out in a Fischer-Tropsch synthesis reactor.

14. A pure phase ε/ε' iron carbide catalyst for Fischer-Tropsch synthesis reaction obtained by the method of claim 1.

15. A Fischer-Tropsch synthesis process comprising: contacting a synthesis feed gas with a catalyst under Fischer-Tropsch synthesis reaction conditions, wherein the catalyst is the pure phase de iron carbide catalyst for Fischer-Tropsch synthesis reaction of claim 14.

16. The process of claim 15, wherein the Fischer-Tropsch synthesis process is carried out in a continuous reactor at a temperature range of 235-250° C., and a pressure range of 2.3-2.5 MPa.

* * * * *